United States Patent [19]

Nealon et al.

[11] Patent Number: 5,112,740
[45] Date of Patent: May 12, 1992

[54] CARBON DIOXIDE ASSAY FOR BODY FLUIDS COMPRISING CARBONIC ANHYDRASE

[75] Inventors: Daniel A. Nealon, Rochester; Richard B. Coolen, Penfield, both of N.Y.

[73] Assignee: Eastman Kodak Company, Rochester, N.Y.

[21] Appl. No.: 451,912

[22] Filed: Dec. 18, 1989

[51] Int. Cl.$^5$ .................. C12Q 1/32; C12Q 9/12; C12N 9/88
[52] U.S. Cl. ...................... 435/15; 435/26; 435/232; 435/194
[58] Field of Search .............. 435/15, 26, 194, 232, 435/969, 970

[56] References Cited

U.S. PATENT DOCUMENTS

| | | | |
|---|---|---|---|
| 3,963,578 | 6/1976 | Aitken et al. | 435/188 |
| 3,974,037 | 8/1976 | Adams | 195/103.5 |
| 3,992,158 | 11/1976 | Przybylowicz | 435/111 |
| 4,144,306 | 3/1979 | Figueras | 435/22 |
| 4,472,498 | 9/1983 | Masuda et al. | 435/7.71 |

Primary Examiner—Douglas W. Robinson
Assistant Examiner—Timothy J. Reardon
Attorney, Agent, or Firm—John R. Everett

[57] ABSTRACT

A multilayer element for assaying carbon dioxide is disclosed. The elememt comprises a spreading layer comprising acetazolamide, a reagent layer comprising phosphoenolpyruvate carboxylase and phosphoenolpyruvate and a registration layer comprising reduced NAD and maleate dehydrogenase.

6 Claims, No Drawings

CARBON DIOXIDE ASSAY FOR BODY FLUIDS COMPRISING CARBONIC ANHYDRASE

FIELD OF THE INVENTION

The present invention relates to clinical chemistry. In particular, it relates to a method and element for the quantitative assay of carbon dioxide in body fluids, such as blood serum.

BACKGROUND OF THE INVENTION

Significant amounts of carbon dioxide are generated by mammals such as humans. In general, only a small portion of the $CO_2$ generated is utilized; the rest is considered waste material and must be eliminated. One means for such elimination is through body fluids, such as the blood stream. The concentration of carbon dioxide in the blood stream has a profound effect on body functions. Thus, the measurement of carbon dioxide content in the blood stream or other body fluids is an important tool for precise and accurate medical diagnosis.

The term carbon dioxide content, as applied to body fluids means the sum of bicarbonate ions, carbonic acid and dissolved carbon dioxide according to the equilibrium $$CO_2 + H_2O \rightleftharpoons H_2CO_3 \rightleftharpoons H^+ + HCO_3^-$$

U.S. Pat. No. 3,974,037 discloses several enzymatic methods for the determination of carbon dioxide in body fluids. These include assays involving either reactions (1), (2), (3) or (4) below, each generating oxalacetate which can be measured with reaction (5) as follows:

$$\text{phosphoenolpyruvate} + HCO_3^- \xrightarrow{\text{PEP carboxylase}} \text{oxaloacetate} + P_i \quad (1)$$

where PEP carboxylase is phosphoenolpyruvate carboxylase and $P_i$ is inorganic phosphorus;

$$ATP + \text{pyruvate} + HCO_3^- \xrightarrow{\text{pyruvate carboxylase}} \text{oxaloacetate} + ADP + P_i; \quad (2)$$

$$\text{phosphoenolpyruvate} + HCO_3^- + ADP \xrightarrow{\text{PEP carboxykinase}} \text{oxaloacetate} + ATP \quad (3)$$

where ADP stands for adenosine diphosphate and ATP stands for adenosine triphosphate. In the reaction defined by (3), the ADP can be replaced by other nucleotide diphosphates depending on the source used to prepare the PEP carboxykinase.

An additional possible enzymatic assay for carbon dioxide is the following reaction involving phosphoenolpyruvate carboxykinase(pyrophosphate) and inorganic phosphorus:

$$\text{phosphoenolpyruvate} + HCO_3^- + P_i \xrightarrow{\text{PEP carboxykinase(pyrophosphate)}} \text{oxalacetate} + PP_i$$

where $PP_i$ stands for inorganic pyrophosphate; and $$\text{oxaloacetate} + NADH + H^+ \xrightarrow{MDH} \text{malate} + NAD^+ \quad (5)$$

where MDH is malate dehydrogenase, NADH is the reduced form of nicotinamide adenine dinucleotide and NAD is the oxidized form.

Each of (1), (2), (3) or (4) when coupled with reaction (5) measures carbon dioxide content either as $CO_2$ or $HCO_3^-$ by determining the concentration change in NADH while maintaining a constant pH. The assay is carried out by mixing all of the reagents required by (1) and (5), (2) and (5), (3) and (5) or (4) and (5) with measured amounts of the body fluid sample, typically a body fluid such as serum or plasma.

When samples of body fluids contain any blood, hemolysis often occurs; that is, the rupture of erythrocytes or red blood cells. The process of hemolysis, therefore, results in the release of all the contents in the erythrocytes including hemoglobin and carbonic anhydrase into the body fluid. Measurement of hemoglobin is, therefore, a direct measure of the extent of hemolysis and is also an indicator of the relative amount of carbonic anhydrase released into the body fluid. Carbonic anhydrase shifts, to a variable extent, the $HCO_3^-$ to $CO_2$ equilibrium in body fluids since it catalyzes the following reaction $$H^+ + HCO_3^- \rightleftharpoons CO_2 + H_2O.$$

Enzymatic measurements for total carbon dioxide using hemolyzed samples using reactions (1)–(4) results in a bias in the assay for the total $CO_2$ as compared to non-hemolysed. The bias is a result of a shift in the equilibrium brought about by carbonic anhydrase. The bias can be negative or positive depending on selected reactions (1)–(4). Normal serum or plasma also contain low levels of circulating carbonic anhydrase which contributes to the random bias seen with existing enzymatic $CO_2$ procedures.

U.S. Pat. No. 3,974,037 teaches that the accuracy of the enzymatic assay procedures disclosed therein can be increased by the addition of carbonic anhydrase to test solutions.

Contrariwise, our research has shown that the presence of carbonic anhydrase, endogenous or added, in body fluids causes unacceptable inaccuracies in an enzymatic assay for total $CO_2$.

SUMMARY OF THE INVENTION

The present invention provides an enzymatic method for the quantitative assay of carbon dioxide ($CO_2$) in body fluid comprising the step of contacting acetazolamide with the fluid.

The present invention also provides a multilayer dry element for the quantitative assay of $CO_2$ in body fluids comprising:

a) a spreading layer comprising acetazolamide and having a pH up to about 9.0, preferably 7.0 to 9.0 when wetted;

b) a reagent layer comprising phosphoenolpyruvate carboxylase and a phosphoenolpyruvate salt; and c) a registration layer comprising reduced nicotinamide adenine dinucleotide and malate dehydrogenase.

The method is based on either enzymatic reaction (1), (2), (3) or (4), coupled with reaction (5). The element is used in carrying out the method when reactions (1) and (5) are involved. When a body fluid sample is applied to the element, the acetazolamide comes in contact therewith.

The inclusion of acetazolamide in enzymatic assays significantly reduces and, in some cases, entirely eliminates the inaccuracy in the amount of $CO_2$ determined caused by the presence of carbonic anhydrase in body fluids.

DETAILS OF THE INVENTION

The amount of reagents used in the assay of this invention are easily determined by those skilled in analytical chemistry, based on teh stoichiometric relations of equations (1) through (5) coupled with the ranges of $CO_2$ normally seen in the body fluid samples being tested. The amount of acetazolamide is in excess to inhibit amounts of carbonic anhydrase which may be encountered in grossly hemolyzed body fluids. Such excess can be established by those skilled in analytical chemistry from the inhibition constant, Ki, of acetazolamide for carbonic anhydrase. Amounts of total carbon dioxide and carbonic anhydrase outside of such ranges can be dealt with by making adjustments based on stoichiometric relations and other adjustments, such as dilution or concentrating a sample, known to analytical chemists.

In general, we have found that acetazolamide will be effective as an inhibitor when a minimum of at least about 0.1 mmol/L is used in a solution assay or at a coverage in the range of about 10 to about 1000 mg/m$^2$ in a dry analytical element.

All of the reagents used in carrying out the necessary enzymatic reactions as defined by (1), (3) and (5) are available commercially. The enzymes of reactions (2) and (4) are obtainable from, for example, university research laboratories.

The solution assay can be carried out by mixing a measured excess of each reagent required by the selected enzymatic chemical equations with a measured amount of body fluid, such as human blood. By excess, we mean an amount of reagent that exceeds the expected stoichiometric amount needed to react with the expected level of total carbon dioxide and/or carbonic anhydrase in the fluid. For example, based on an enzymatic assay conducted according to equations (1) and (5), one would mix, at a start pH (probably 6.5 to 10.5) measured excess amounts of phosphoenolpyruvate, phosphoenolpyruvate carboxylase, malate dehydrogenase, NADH and acetazolamide with a measured amount of the sample body fluid.

The change in the concentration of NADH is directly proportional to the decrease in absorbance of light between 290 and 380 nm, preferably 340 nm, at a constant temperature between 25° and 45° C. and a constant pH, usually between about 6.5 and about 10.5. NADH concentration can be measured readily by those skilled in the art using conventional spectrophotometric procedures. The change in the concentration of NADH is proportional to the formation of oxaloacetate. The formation of oxaloacetate is a function of the concentration of bicarbonate in the system. Thus the change in absorbance at 340 nm can be used as a direct measure of the original concentration of bicarbonate in the sample fluid.

It should also be understood that other wavelengths, e.g. 366 nm, can be used for the foregoing purpose. Furthermore, the enzyme systems can be coupled with a redox-dye system which will change the wavelength at which the absorbance measurement can be made.

The dry multilayer test element provided by this invention comprises one or more reagent zones or layers and registration zones or layers. All reference hereinafter to layers also refers to zones. In one embodiment of the invention, the element also comprises one or more buffer layers between the reagent layer(s) and the registration layer(s). The layers of the element may be self-supporting, but are preferably on a support. The reagent layer is preferably permeable and porous. Permeability, including permeability arising from porosity, can be achieved through the presence of various carriers, matrices, or binders, such as fibrous materials or porous, non-fibrous materials described in U.S. Pat. No. 4,144,306. A preferred permeable binder of the invention is the above-described class of blushed polymers. Also useful as a porous carrier is a polymer binder with an inert particulate material, such as microcrystalline cellulose, dispersed therein. Pigment particles may be incorporated in the reagent layer for light reflecting purposes.

Registration layers are described in the above-referenced U.S. Pat. No. 4,144,306. The registration layer is permeable to oxalacetate diffusing from the reagent layer to allow spectrophotometric determination of NADH between 290 and 380 nm. The registration layer is adapted to receive diffusible material from the reagent layer.

The preferred elements of the present invention include a spreading layer, a subbing layer, a reagent layer, a registration layer or a combination registration/reagent layer. The composition of these layers and their location in the element are known in the art and are described in U.S. Pat. No. 3,992,158 and the above referenced U.S. Pat. No. 4,144,306 are incorporated herein by reference. For example, spreading layers can be isotropically porous, achieving such porosity through the use of inert particle materials and/or blush polymers, and can be positioned adjacent to the reagent layer as the outermost layer of the element (if a multilayer element is used). Any of the layers of the present invention may also include well-known addenda, such as buffers, surfactants, or coating aids, as described in the above-referenced U.S. Pat. No. 4,144,306.

Multilayer elements of the invention can be prepared by various laminating or coating techniques well-known in the art, such as hand-coating, blade coating, bead coating, or dip coating. The elements may be self-supporting or carried on a support. Useful support materials include a variety of polymeric materials, such as cellulose acetate, poly(ethyleneterephthalate), polycarbonates, and polyvinyl compounds such as polystyrenes. The support is radiation transmissive between 290 to 380 nm. Coating and laminating techniques, along with support materials, are further described in the above-referenced U.S. Pat. No. 4,144,306.

For coatable reagent layers, a coating solution or dispersion including a binder and coated as discussed herein and dried to form a dimensionally stable zone. The thickness of any reagent layer and its degree of permeability are widely variable and depend on actual usage. Dry thicknesses of from about 10 to about 100 mµ are convenient, although more widely varying thicknesses can be used. Fibrous reagent layers can be formed by impregnation of a fibrous matrix, in accordance with well-known techniques.

Registration layers and other layers can be prepared using methods and thicknesses as used when preparing coatable reagent layers, but with constituents appropriate for the particular layer.

The elements of the invention are used by applying a sample of body fluid to be assayed to the element. Generally, the element will be formed so that the liquid first contacts one or more spreading layers or zones. After application of the liquid, the element may be exposed to any conditioning, such as heating or humidification, that is desirable to quicken or otherwise facilitate any test result.

After an appropriate time to allow for diffusion of the sample from the spreading layer and diffusion of the oxalacetate produced in the reagent layer to the registration layer of oxalacetate and the reaction of the oxaloacetate with NADH, the amount of detectable material in the registration zone is determined spectrophotometrically. Such a determination may be made by passing the element through an area in which an apparatus suitable for reflection or transmission spectrophotometry is provided.

Such apparatus serves to direct a beam of energy, such as light, through the support and the reagent and registration layers. The light is then reflected back to a detecting means or passes through the element to a detector, in the case of transmission detection. Use of reflection spectrophotometry can be advantageous in some situations as it can effectively avoid interference from residues, such as blood cells, which may be left on or in the zones of the element.

When blood serum is tested or means are provided for eliminating unwanted whole blood residues, transmission techniques can be used to detect and quantify the NADH by directing a flow of U.V. radiation at one surface of the element and measuring the output of that energy from the opposing surface of the element. Various calibration techniques can be used to provide a control for the analysis. As one example, a sample of a standard test liquid can be applied adjacent to the area where the drop of sample is placed in order to permit the use of differential measurements in the analysis.

EXAMPLE 1

This example shows that hemolysis indeed causes a negative bias with prior art enzymatic $CO_2$ procedures (U.S. Pat. No. 3,974,037).

A stock hemolysate solution was prepared by collecting fresh blood from suitable human donors. The erythrocytes of the blood was pooled, and then washed with saline four times. The erythrocytes were then lysed by five cycles of freezing to $-70°$ C. and thawing at $37°$ C. The resulting hemolysate was filtered through Whatman No. 1 (Whatman Ltd. UK) filter paper. Hemoglobin concentration in mg/dL was determined by the method of Harboe described in *Sca. J. Clinical Lab. Invest. II* pp. 66–70, 1959. The concentration of hemoglobin is directly related to the level of carbonic anhydrase in the hemolysate stock solution.

A stock solution of 50 mmol/L bicarbonate (4.2 g $NaHCO_3$/L) was prepared in 100 mmol/L tricine (17.92 g tricine/L) buffer (pH 8.0). Other buffers may also be used. This stock bicarbonate was diluted with either (a) the buffer or (b) the stock hemolysate solution and the buffer to give test solution samples of about 25 mmol/L $HCO_3^-$ and varying concentrations of hemoglobin, as a measure of the amount of carbonic anhydrase present.

Reference values for $CO_2$ (Table I) on test samples were determined using a thermal conductivity procedure on the Corning 965 carbon dioxide analyzer. The technology of the reference procedure is such that it is not affected by carbonic anhydrase. The procedure is described in *J. Biol. Chem.*, 61:523, 1924.

The enzymatic values for $CO_2$ were determined on the test samples with dry-chemistry slides on an EKTACHEM Clinical Chemistry Analyzer (available from Eastman Kodak Company, Rochester, N.Y.). The principle of the assay is as represented above by reaction series (1) and (5). It will be clear to those skilled in the art that the element of this invention can be readily adapted to any one of reactions (2) to (4). This dry element did not include a carbonic anhydrase inhibitor. It had the following format:

| | FIGURE 1 | | |
|---|---|---|---|
| | | Dry Amount Coverage (/m²) | Range (/m²) |
| Spreading Layer | Barium Sulfate | 108.592 g | 50–250 g |
| | Cellulose Acetate | 8.629 g | 2.0–10.0 g |
| | Triton X-405 Surfactant | 2.159 g | 0.5–5.0 g |
| | Tris(hydroxymethyl)-aminomethane (THAM) | 1.385 g | 0.0–5.0 g |
| | Tris hydrochloride (Tris HCl) | 1.203 g | 0.0–5.0 g |
| | Estane Resin | 1.082 g | 1.0–5.0 g |
| Subbing Layer | N-vinylpyrrolidone (PVP) | 1.070 g | 0.3–5.0 g |
| Reagent Layer | Gelatin | 10.0 g | 1.0–20.0 g |
| | Alkanol XC Surfactant | 0.1 g | 0.05–2.5 g |
| | Zonyl FSN Surfactant | 0.02 g | 0.01–2.5 g |
| | $MgSO_4$ | 0.50 g | 0.1–5.0 g |
| | Tricine | 3.401 g | 0.5–5.0 g |
| | Phosphoenolpyruvate | 3.25 g | 2.5–10.0 g |
| | Phosphoenolpyruvate Carboxylase | 1524 U | 1,000–20,000 U |
| Registration Layer | Gelatin | 7.14 g | 1.0–20.0 g |
| | Alkanol XC Surfactant | 0.1 g | 0.05–2.5 g |
| | Zonyl FSN Surfactant | 0.020 g | 0.01–2.5 g |
| | Bis(vinylsulfonyl-methyl)ether (BVSME) | 0.173 g | 0–2.5 g |
| | Tricine | 3.401 g | 0.5–5.0 g |

-continued

FIGURE 1

|      | Dry Amount Coverage (/m$^2$) | Range (/m$^2$) |
|------|------------------------------|----------------|
| NADH | 3.0 g                        | 2.0–5.0 g      |
| MDH  | 1076 U                       | 1,000–30,000 U |

TABLE I

| Test Sample No. | Hemoglobin (mg/dL) | Bicarbonate (mmol/L) Reference | Bicarbonate (mmol/L) Enzymatic | Bias (mmol/L) |
|---|---|---|---|---|
| 1 | 0   | 24.3 | 23.3 | −1.0 |
| 2 | 2   | 24.1 | 22.9 | −1.2 |
| 3 | 4   | 24.2 | 22.9 | −1.3 |
| 4 | 6   | 23.9 | 21.7 | −2.2 |
| 5 | 10  | 24.0 | 22.1 | −1.9 |
| 6 | 26  | 24.1 | 20.2 | −3.9 |
| 7 | 70  | 24.3 | 16.8 | −7.5 |
| 8 | 247 | 23.9 | 15.7 | −8.2 |
| 9 | 400 | 23.1 | 14.0 | −9.1 |

As the level of carbonic anhydrase increased, as indicated by the increasing hemoglobin concentrations in the test solutions, there was an increasing negative bias in the enzymatic assay as compared to the reference values. The bias becomes significant at about 6 mg/dL hemoglobin.

EXAMPLE 2

This example confirms that the negative bias seen in Example 1 is due to carbonic anhydrase.

A stock solution of 50 mmol/L of bicarbonate was diluted with the 100 mmol/L tricine buffer to give an approximately 25 mmol/L solution of bicarbonate. To this solution was added purified carbonic anhydrase (Sigma Chemical Co.) The bicarbonate stock solution, without carbonic anhydrase, served as the control.

TABLE II

|                         | Bicarbonate (mmol/L) Reference | Bicarbonate (mmol/L) Enzymatic | Bias (mmol/L) |
|-------------------------|---|---|---|
| Control                 | 22.3 | 22.1 | −0.2  |
| Added Carbonic Anhydrase | 22.0 | 10.8 | −11.2 |

Thus, the bias seen in example 1 is due to carbonic anhydrase released from the erythrocytes during hemolysis.

EXAMPLE 3

This example demonstrates the effectiveness of acetazolamide in inhibiting the carbonic anhydrase bias in enzymatic assays for $CO_2$.

A number of carbonic anhydrase inhibitors were tested. All are commercially available.

A stock solution of 50 mmol/L bicarbonate was prepared in 100 mmol/L tricine buffer (pH 8.0). The stock bicarbonate was diluted with either (a) buffer alone containing the test carbonic anhydrase inhibitor (internal control) or (b) with buffer containing the carbonic anhydrase inhibitor and diluted stock hemolysate to give a final hemoglobin concentration of 200 mg/dL. All solutions were incubated at room temperature for 1 hour and then spotted, as a sample, on to the enzymatic $CO_2$ slide used in example 1. The results are reported in Table III.

TABLE III

| Inhibitor | Final Inhibitor Concentration (mmol/L) | Enzymatic Bicarbonate (mmol/L) Without Hemolysate | Enzymatic Bicarbonate (mmol/L) With Hemolysate | Bias (mmol/L) |
|---|---|---|---|---|
| None           | —    | 22.3 | 15.9 | −6.4 |
| Azide          | 2.5  | 23.3 | 16.5 | −6.8 |
| Thiocyanate    | 2.5  | 22.0 | 15.3 | −6.7 |
| Glycine        | 20.0 | 22.4 | 14.3 | −8.1 |
| DL-Alanine     | 20.0 | 22.9 | 14.3 | −8.6 |
| HEDTA*         | 5.0  | 23.3 | 15.7 | −7.6 |
| EDTA*          | 5.0  | 22.8 | 14.7 | −8.1 |
| Cyanide        | 2.5  | 22.5 | 18.7 | −3.8 |
| Dithioerythritol | 5.0 | 23.3 | 17.5 | −5.8 |
| Sulfanilamide  | 2.0  | 22.8 | 14.9 | −7.9 |
| Sulfathiazole  | 2.0  | 24.2 | 15.8 | −8.4 |
| Acetazolamide  | 1.0  | 23.2 | 22.9 | −0.3 |

*HEDTA: N-Hydroxyethylethylenediaminetriacetic acid
EDTA: Ethylenediaminetetraacetic acid Among the carbonic anhydrase inhibitors tested, acetazolamide was the most effective in eliminating the negative bias the enzymatic $CO_2$ assay.

EXAMPLE 4

Inclusion of acetazolamide in the enzymatic $CO_2$ dry chemistry element significantly reduces the bias seen with freshly prepared hemolysates.

Acetazolamide was included in the spreading layer of an enzymatic $CO_2$ dry element as described in example 1. The acetazolamide is equally as effective when included in the reagent layer.

A stock solution of 50 mmol/L bicarbonate was prepared in 100 mmol/L tricine buffer (pH 8.0). The stock bicarbonate was diluted with either (a) the buffer or (b) the stock hemolysate and the buffer to give test solutions of about 25 mmol/L $HCO_3^-$ and varying concentrations of hemoglobin. The test solutions were spotted on elements not containing acetazolamide (as defined in example 1) and onto elements containing acetazolamide in the spreading layer. Assay results were compared to the bicarbonate values obtained with the reference $CO_2$ method referred to in example 1 to obtain a measure of the bias.

TABLE IV

| Hemoglobin Concentration (mg/dL) | Bicarbonate Bias (mmol/L) | |
| --- | --- | --- |
| | Element Without Acetazolamide | Element With Acetazolamide |
| 0 | 0.61 | −0.83 |
| 25 | −3.59 | −1.44 |
| 55 | −4.39 | −1.44 |
| 112 | −5.39 | −1.94 |
| 223 | −5.70 | −1.96 |
| 263 | −6.37 | −1.76 |

EXAMPLE 5

This example shows that inclusion of acetazolamide in the enzymatic $CO_2$ dry chemistry element effectively eliminates the bias seen with hemolyzed and apparently non-hemolysed patient samples.

Visibly hemolyzed and apparently non-hemolysed patient samples were analyzed for $CO_2$ by spotting on analytical elements with and without acetazolamide. Values were compared to those obtained with the reference $CO_2$ method as defined in example 1. Hemoglobin was quantitated in each sample by the method as defined in Example 1.

TABLE V

| Patient Sample No. | Hemoglobin Concentration (mg/dL) | Bicarbonate Bias (mmol/L) | |
| --- | --- | --- | --- |
| | | Element Without Acetazolamide | Element With Acetazolamide |
| 1 | 3 | −0.71 | −0.17 |
| 2 | 5 | −2.22 | 1.12 |
| 3 | 12 | −1.29 | 0.16 |
| 4 | 25 | −1.63 | −0.45 |
| 5 | 53 | −3.11 | 0.29 |
| 6 | 86 | −3.57 | −0.20 |
| 7 | 116 | −2.59 | −0.27 |
| 8 | 129 | −0.96 | −0.18 |
| 9 | 188 | −4.23 | −0.14 |

The invention has been described in detail with particular reference to preferred embodiments thereof, but it will be understood that variations and modifications can be effected within the spirit and scope of the invention.

We claim:

1. A multilayer dry element for the quantitative assay of $CO_2$ in body fluids comprising:
   a) a spreading layer comprising at least 10 $mg/M^2$ of acetazolamide and having a pH in the range 7.0 to 9.0;
   b) a reagent layer comprising phosphoenolpyruvate carboxylase and a phosphoenolpyruvate salt;
   c) a registration layer comprising reduced nicotinamide adenine dinucleotide and malate dehydrogenase.

2. A multilayer dry element for the quantitative assay of $CO_2$ in body fluids comprising:
   a) a spreading layer comprising at least 10 $mg/M^2$ of acetazolamide and having a pH in the range 7.0 to 9.0;
   b) a reagent layer comprising pyruvate carboxylase and pyruvate;
   c) a registration layer comprising reduced nicotinamide adenine dinucleotide and malate dehydrogenase.

3. A multilayer dry element for the quantitative assay of $CO_2$ in body fluids comprising:
   a) a spreading layer comprising at least 10 $mg/M^2$ of acetazolamide and having a pH in the range 7.0 to 9.0;
   b) a reagent layer comprising phosphoenolpyruvate carboxykinase, phosphoenolpyruvate and inorganic phosphorus;
   c) a registration layer comprising reduced nicotinamide adenine dinucleotide and malate dehydrogenase.

4. A multilayer dry element for the quantitative assay of $CO_2$ in body fluids comprising:
   a) a spreading layer comprising at least 10 $mg/M^2$ of acetazolamide and having a pH in the range 7.0 to 9.0;
   b) a reagent layer comprising phosphoenolpyruvate carboxykinase and phosphoenolpyruvate;
   c) a registration layer comprising reduced nicotinamide adenine dinucleotide and malate dehydrogenase.

5. The element of claim 1, 2, 3 or 4 wherein the reagent layer and the registration layer is combined.

6. The element of claim 1, 2, 3 or 4 wherein the acetazolamide coverage is in the range of 10 to 1000 $mg/M^2$.

* * * * *